(12) United States Patent
Brunetti et al.

(10) Patent No.: US 11,828,388 B2
(45) Date of Patent: Nov. 28, 2023

(54) NEEDLE-FREE CONNECTOR

(71) Applicants: Bruce Brunetti, Phillipsburg, NJ (US); James Nixon, Allentown, PA (US); Gail Bogert, Macungie, PA (US)

(72) Inventors: Bruce Brunetti, Phillipsburg, NJ (US); James Nixon, Allentown, PA (US); Gail Bogert, Macungie, PA (US)

(73) Assignee: B. Braun Medical Inc., Bethlehem, PA (US)

( * ) Notice: Subject to any disclaimer, the term of this patent is extended or adjusted under 35 U.S.C. 154(b) by 0 days.

(21) Appl. No.: 17/689,428

(22) Filed: Mar. 8, 2022

(65) Prior Publication Data
US 2023/0288005 A1 Sep. 14, 2023

(51) Int. Cl.
F16L 37/40 (2006.01)
A61M 39/10 (2006.01)
B60K 15/035 (2006.01)

(52) U.S. Cl.
CPC ............. F16L 37/40 (2013.01); A61M 39/10 (2013.01); *B60K 15/03519* (2013.01); *B60K 2015/03538* (2013.01)

(58) Field of Classification Search
CPC ................................ F16L 37/40; A61M 39/10
See application file for complete search history.

(56) References Cited

U.S. PATENT DOCUMENTS

| | | | |
|---|---|---|---|
| 3,831,629 A * | 8/1974 | Mackal | F16K 15/14 604/920 |
| 5,122,123 A * | 6/1992 | Vaillancourt | A61M 39/14 604/905 |
| 7,510,545 B2 | 3/2009 | Peppel | |
| 7,520,489 B2 | 4/2009 | Ruschke et al. | |
| 7,784,766 B2 | 8/2010 | Guala | |
| 8,298,196 B1 | 10/2012 | Mansour | |
| 8,408,226 B2 | 4/2013 | Raines et al. | |
| 8,636,720 B2 | 1/2014 | Truitt et al. | |
| 8,708,976 B1 | 4/2014 | Yeh et al. | |
| 8,715,247 B2 | 5/2014 | Mansour et al. | |
| 9,089,682 B2 | 7/2015 | Yeh et al. | |
| 9,855,412 B2 | 1/2018 | Chen et al. | |
| 10,653,879 B2 * | 5/2020 | Mansour | A61M 39/22 |
| 2006/0161115 A1 * | 7/2006 | Fangrow | A61M 39/26 604/249 |
| 2011/0319859 A1 * | 12/2011 | Zeytoonian | A61M 39/045 604/246 |
| 2016/0228687 A1 | 8/2016 | Chih et al. | |
| 2018/0214684 A1 * | 8/2018 | Avula | A61L 2/186 |
| 2019/0269898 A1 * | 9/2019 | Pütter | A61M 39/10 |

* cited by examiner

*Primary Examiner* — Patrick C Williams
(74) *Attorney, Agent, or Firm* — Christopher A. Rothe; Culhane Meadows PLLC

(57) ABSTRACT

A needle-free connector for accessing a patient's intravenous line includes a hollow body having a first end with a first opening, a second end with a second opening, and an inner wall defining a chamber. A hollow piston disposed in the chamber is axially collapsible to allow fluid to flow between the inner wall of the hollow body and the outer surface of the hollow piston. An inner surface of the hollow piston includes a fluted section having a radial array of axial slots. The fluted section has a first radial thickness configured to buckle in response to axial force applied to the hollow piston. The hollow piston further includes a retrograde-reducing stiffener. The retrograde-reducing stiffener has a second radial thickness that is greater than the first radial thickness.

30 Claims, 6 Drawing Sheets

NEEDLE-FREE CONNECTOR

FIELD

The present invention relates generally to fluid connectors used in the medical industry, and more specifically to a fluid connector or valve that provides access to a patient's intravenous line and reduces or prevents unwanted migration of fluid in response to incidental changes in pressure in the line.

BACKGROUND

A needle-free connector (or "NFC") is a device used in the medical industry for accessing a patient's intravenous line and administering fluid to the patient. Some NFCs feature a hollow body forming a chamber and a movable plug or valve element inside the chamber. The valve element regulates the flow of fluid through the NFC.

The body has a first end that can be connected to a fluid source and a second end that can be connected to an intravenous line. The intravenous line, in turn, is connected to a catheter that accesses a patient's blood vessel. In many cases, the fluid source is a needleless syringe. The valve element is formed of a resilient flexible material that allows the valve element to change shape in response to external force applied to the valve element from a fluid source. As such, the valve element is displaceable or deformable between a sealed state that prevents the flow of fluid through the NFC and an open or unsealed state that allows the flow of fluid through the NFC.

Connection and disconnection of an NFC to and from a fluid source or IV tubing can cause changes in pressure in the chamber. A negative change in pressure can draw residual fluid from the intravenous line into the NFC, and draw blood from the patient into the catheter. A positive change in pressure can expel residual fluid from the NFC into the intravenous line, and push residual fluid in the intravenous line into the catheter and patient. This flow of residual fluid in response to pressure changes in the NFC is referred to as "displacement". "Positive displacement", as used herein, refers to the flow of residual fluid out of or away from the NFC, and "negative displacement", as used herein, refers to the flow of residual fluid into or toward the NFC. The type of displacement that occurs can be influenced by how the valve element is designed and how it responds to changes in fluid pressure.

In some NFCs, the disconnection of a fluid source causes a net increase in pressure in the chamber, causing residual fluid in the NFC to discharge from the second end into the intravenous line. These devices are referred to herein as "positive displacement NFCs". In other NFCs, the disconnection of a fluid source causes a net decrease in pressure in the NFC, causing blood and other fluid from the intravenous line to flow into or toward the second end of the NFC. These devices are referred to herein as "negative displacement NFCs".

Positive displacement NFCs have the desirable effect of flushing out the NFC and catheter after an injection. This prevents residual blood from remaining in, or backing up into, the NFC or catheter when the fluid source is disconnected. Flushing out the NFC and catheter after an injection prevents occlusions from forming in the NFC and catheter and reduces the risk of central-line associated bloodstream infections (CLABSI) caused by bacterial growth.

The ability of the valve element to collapse in response to pressure increases in the NFC can cause a problem called "retrograde". The term "retrograde", as used herein, refers to an incidental and undesired migration or flow of fluid in the patient's intravenous line toward or into the NFC. Retrograde can be caused by a contraction and expansion of the valve element in response to a patient's sudden movement, the patient's blood pressure/pulse, an impact force, or diffusion.

The medical device industry has identified applications where a certain amount of positive displacement is desirable. To meet ever changing demands, it is highly desirable to control the amount of positive displacement during the manufacture of NFCs. Unfortunately, the magnitude of displacement and retrograde are extremely sensitive to changes made to the valve element and body. Slight modifications to some variables can create dramatically different and unpredictable changes in displacement and/or retrograde. In addition, a small adjustment to a first variable might lead to undesired performance and require adjustment to a second variable to counterbalance the adverse effect of changing the first variable.

In the current state of the art, there is a need for an NFC that provides a desired amount of positive displacement with minimal or no retrograde. There is also a need for an NFC design that allows for accurate, consistent and cost-effective modification to control the amount of retrograde with repeatable results. Unfortunately, manufacturers have not identified the design parameters that allow them to control the magnitude of displacement while reducing retrograde in a consistent manner. As such, existing NFC designs and manufacturing techniques do not allow manufacturers to produce NFCs that provide both a desired amount of displacement and a consistent reduction in retrograde.

SUMMARY

NFCs according to the present disclosure provide desired amounts of displacement with consistent reductions in retrograde.

In one example, a needle-free connector for accessing a patient's intravenous line includes a hollow body having a first end with a first opening, a second end with a second opening, and an inner wall defining a chamber. A hollow piston, which is disposed in the chamber, has an inner surface, an outer surface, a longitudinal axis and a void inside the hollow piston. The hollow piston is axially collapsible in the chamber to allow fluid to flow between the inner wall of the hollow body and the outer surface of the hollow piston.

In the same example, or a different example, the inner surface of the hollow piston can include a fluted section having a radial array of axial slots that extend parallel to the longitudinal axis. The fluted section can include a first radial thickness that is configured to buckle in response to axial force applied to the hollow piston. The hollow piston can further include a retrograde-reducing stiffener. The retrograde-reducing stiffener can include a second radial thickness that is greater than the first radial thickness.

In the same example, or a different example, the fluted section has axial slots that each define a wing-shaped recess extending radially outwardly from the longitudinal axis.

In the same example, or a different example, the void can extend from a base end of the hollow piston to a midsection of the hollow piston.

In the same example, or a different example, the inner surface of the hollow piston and the outer surface of the hollow piston can define a wall section that circumferentially surrounds the void.

In the same example, or a different example, the fluted section can include a first portion of the wall section, and the retrograde-reducing stiffener can include a second portion of the wall section.

In the same example, or a different example, the retrograde-reducing stiffener can extend between the base end of the hollow piston and the fluted section.

In the same example, or a different example, the fluted section can extend from the base end of the hollow piston to the midsection of the hollow piston.

In the same example, or a different example, the retrograde-reducing stiffener includes a resilient member housed inside of the void.

In the same example, or a different example, the resilient member can be made of foam.

In the same example, or a different example, the resilient member can be cylindrical.

In the same example, or a different example, the resilient member can have an axial length and a diameter, the axial length being greater than the diameter.

In the same example, or a different example, the hollow piston can include a sealing end opposite the base end.

In the same example, or a different example, the sealing end can be movable in the chamber to a sealing state in which the sealing end fluidly seals the first opening of the hollow body to prevent fluid flow through the first end.

In the same example, or a different example, the sealing end can be movable out of the sealing state and into an open state, the sealing end being moved away from the first opening in the open state to permit fluid flow through the first end.

In the same example, or a different example, the sealing end can include at least one slit that opens in response to axial force applied to the hollow piston.

In the same example, or a different example, the hollow body can be made of thermoplastic resin.

In the same example, or a different example, the hollow piston can be made of silicon rubber.

In the same example, or a different example, the inner wall can form an annular ring that extends radially inwardly from the inner wall.

In the same example, or a different example, the annular ring can include at least a portion of the retrograde-reducing stiffener.

In the same example, or a different example, the inner surface can taper radially inwardly toward the longitudinal axis along a length of the void.

BRIEF DESCRIPTION OF THE DRAWINGS

The summary and detailed description sections will be better appreciated when reviewed in conjunction with the drawing figures. The drawing figures illustrate exemplary and non-limiting embodiments, and depict elements which can be combined and arranged either as shown, or in any other combination and/or arrangement contemplated by persons having ordinary skill in the art.

DETAILED DESCRIPTION

Figure 1:
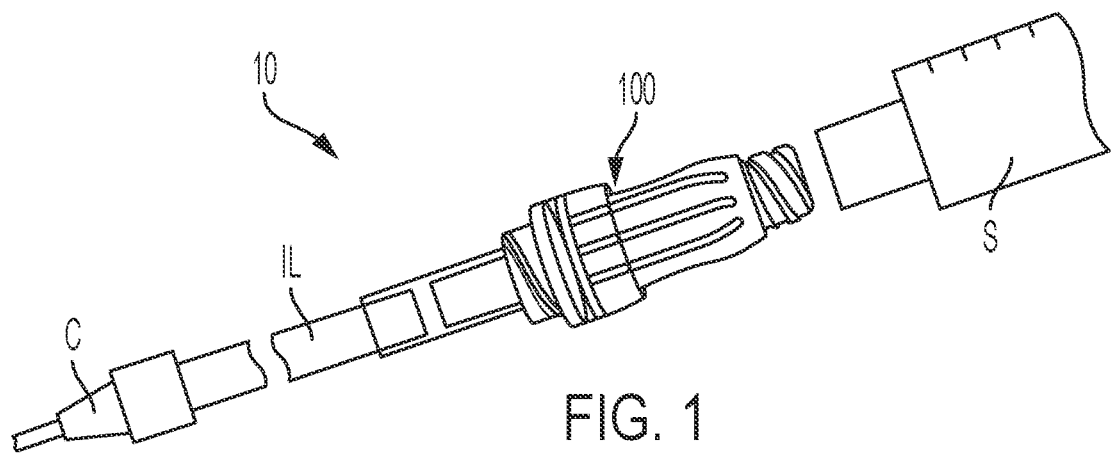
FIG. 1 is a truncated perspective view of a system featuring an NFC according to one example.

Referring to FIG. 1, a system 10 is shown that features a NFC 100 according to one embodiment. System 10 includes NFC 100, an intravenous line IL, a catheter C, and a fluid source S. Fluid source S is a needleless syringe in the present example but can be other types of containers that supply fluid. NFC 100 is configured to attach to and provide fluid access to intravenous line IL. Once NFC 100 is attached to intravenous line IL, fluid from fluid source S can be delivered through the NFC, intravenous line IL, and catheter C into a patient's bloodstream.

Figure 2:
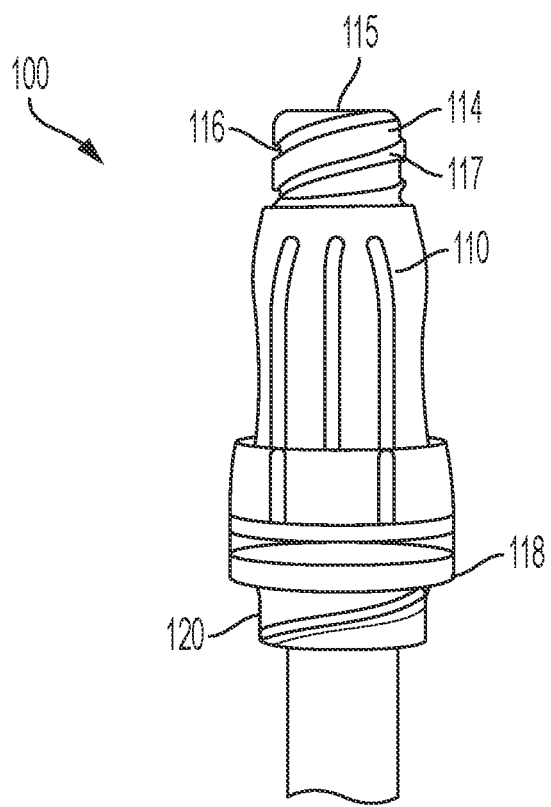
FIG. 2 is an elevation view of the NFC shown in FIG. 1.
Figure 3:
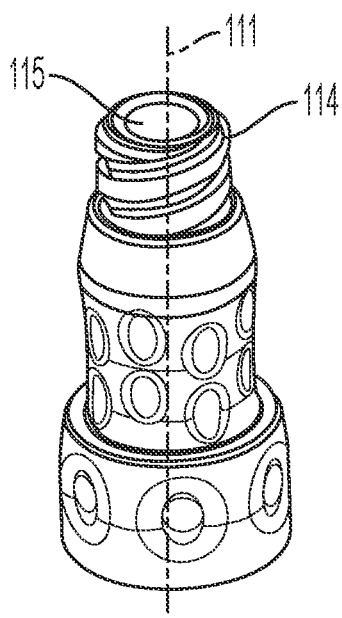
FIG. 3 is a perspective view of a body portion of the NFC shown in FIG. 1.
Figure 4:
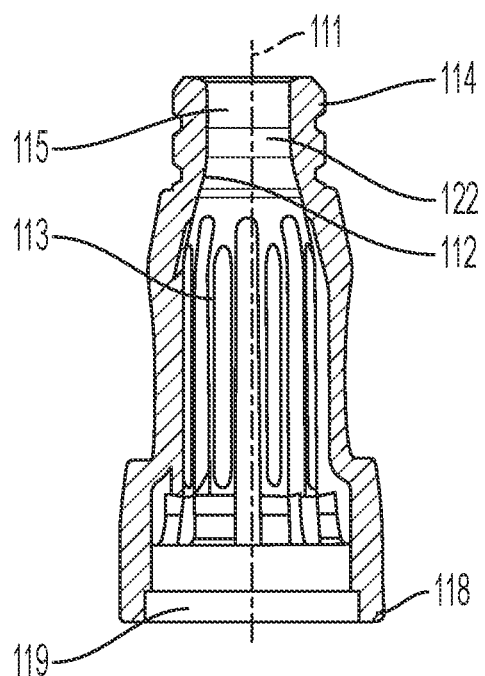
FIG. 4 is a cross section view of the body portion of the NFC shown in FIG. 1.

Referring to FIGS. 2-4, NFC 100 has a hollow housing or body 110 formed of a relatively rigid material, such as a thermoplastic resin. Body 110 has a first end 114 with a first opening 115. First end 114 includes a first connector 116 configured to connect to fluid source S. First connector 116 includes an external thread 117 that mates with an internal thread on fluid source S to connect NFC 100 to the fluid source in a fluid tight connection. Body 110 also has a second end 118 with a second opening 119 opposite first end 114 and first opening 115. Second end 118 includes a second connector 120 configured to connect to intravenous line IL.

Body 110 has a longitudinal axis 111 and a fixed inner wall 112 that defines a chamber 113. First opening 115 connects to a throat section or passage 122 that leads into chamber 113. Throat section 122 has an hour-glass shaped geometry that transitions from a widened diameter section at first opening 115 to a slightly narrower diameter section, and then widens again as the throat section extends further into chamber 113 and towards second end 118, as shown.

Figure 5:
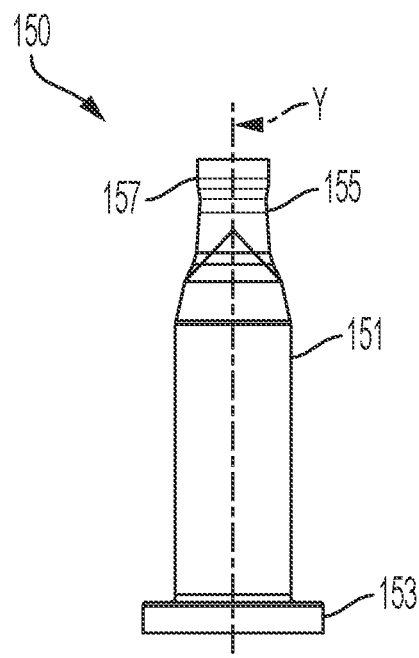
FIG. 5 is an elevation view of a piston element of the NFC shown in FIG. 1.
Figure 6A:
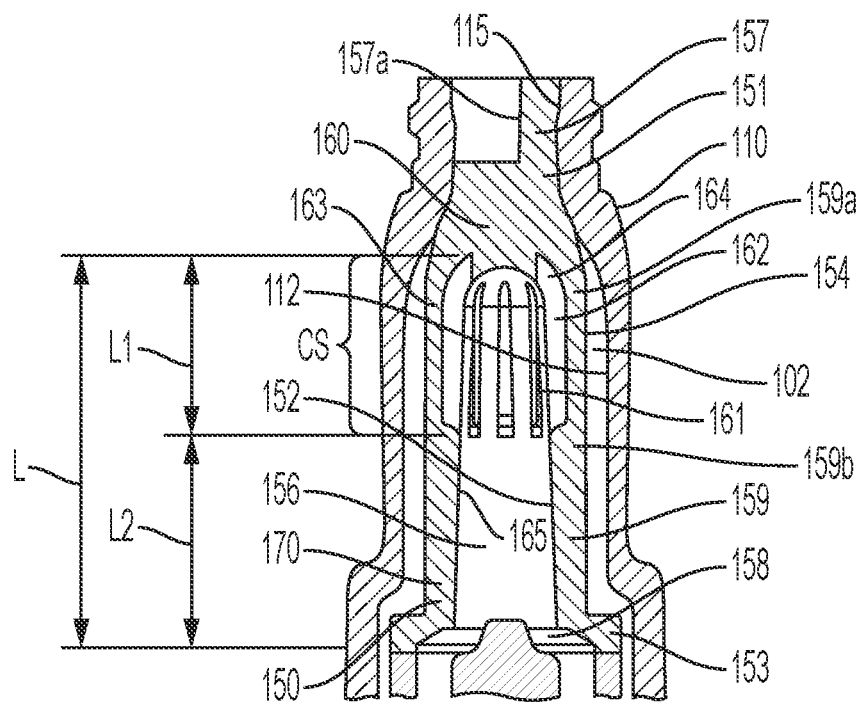
FIG. 6A is a truncated cross section view of the NFC shown in FIG. 1, showing the piston element in a sealing state.
Figure 6B:
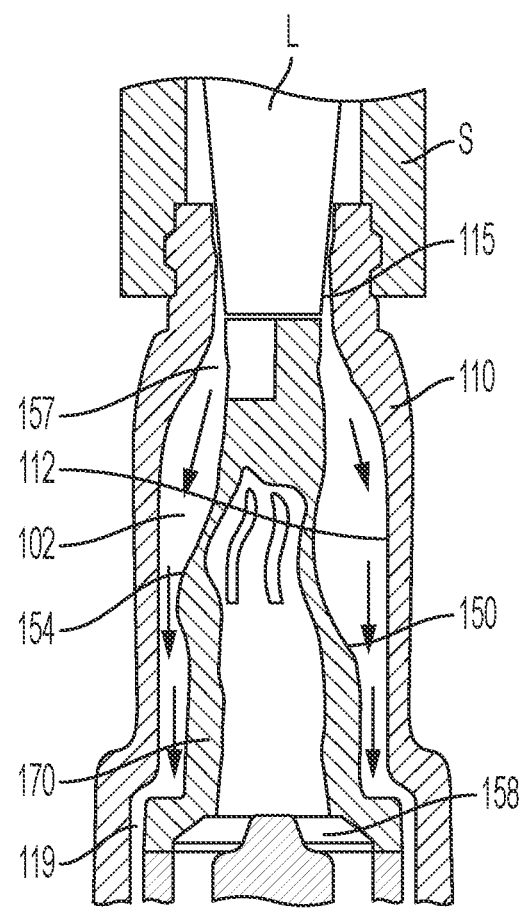
FIG. 6B is a truncated cross section view of the NFC shown in FIG. 1, showing the piston element in an open state.

NFC 100 further includes a hollow piston mounted inside body 110. Referring to FIGS. 5, 6A and 6B, a hollow piston 150 is shown according to one embodiment. Piston 150 has a piston body 151 formed of a resilient flexible material, such as silicon rubber. Piston body 151 has an inner surface 152, an outer surface 154, a longitudinal axis Y and a central void 156 inside the inner wall. Inner surface 152 tapers radially inwardly toward longitudinal axis Y along the length of void 156 as shown. Inner wall 112 of body 110 and outer surface 154 of piston 150 form a space or "inner volume" that provides a fluid passage 102 through NFC 100.

Piston 150 has a bottle-shaped geometry featuring a base end 153 and a neck 155. Neck 155 forms a sealing end 157 opposite base end 153. Sealing end 157 has a geometry in the sealing state that conforms to the hour-glass shaped geometry of throat section 122 of body 110. This conforming geometry provides a fluid tight seal. Sealing end 157 also defines at least one slit 157a that opens when fluid source S is introduced into first opening 115.

When fluid source S is introduced into first opening 115, the fluid source contacts and mechanically collapses sealing end 157, which causes the at least one slit 157a to open. Fluid source S may have a male Luer or similar geometry configured to enter first opening 115 and collapse sealing end 157. Base end 153 of piston 150 forms an opening 158 that opens into a central void 156 inside piston 150.

Pistons according to the present disclosure are elastically deformable in response to a axial compression caused by contact with a fluid source. The term "elastically deformable" or "elastic deformability", as used herein, means the ability to buckle, collapse, bend, or otherwise change shape when subjected to axial compression, and then return to an original shape or state when the compressive force is partially or completely removed.

In the present example, piston 150 is elastically deformable in body 110 between a sealing state and an open state. In the sealing state, shown in FIG. 6A, piston 150 is in a relaxed state in which body 151 maintains its original shape without deformation. In this state, sealing end 157 is received in first opening 115 and seals the first opening. In the open state, shown in FIG. 6B, piston 150 is axially deformed and collapsed by a male Luer portion L of fluid source S. Luer portion L axially compresses sealing end 157 and moves the sealing end out of first opening 115. This mechanical collapse unseals first opening 115 and causes slit 157a to open, creating a fluid path. The fluid path allows fluid to flow through first opening 115 and into fluid passage 102, as represented by the arrows. The fluid flows between inner wall 112 of body 110 and outer surface 154 of the piston and exits second opening 119.

Pistons according to the present disclosure include one or more areas of minimum wall thickness, as measured between the inner surface and outer surface of the piston. The area(s) of minimum wall thickness extend axially, or parallel to the longitudinal axis, along the length of the void. These areas of the piston are the areas most prone to buckling or collapse when male Luer portion L is inserted into first opening 115 and displaces sealing end 157. As such, the areas of minimum wall thickness influence how and to what extent the piston changes shape in response to axial compression, and how the piston returns to its original shape when axial compressive force is removed.

Pistons according to the present disclosure also include one or more retrograde-reducing stiffeners to prevent or minimize retrograde when the piston returns to its original shape. The retrograde-reducing stiffeners limit the amount of deformation that a piston undergoes in response to pressure increases and decreases in the chamber.

Referring again to FIG. 6A, inner surface 152 and outer surface 154 of piston 150 define a wall section 159 that circumferentially surrounds void 156. Wall section 159 has a first portion 159a with areas of minimum wall thickness, and a second portion 159b with a wall thickness significantly greater than the minimum wall thickness. First portion 159a has an axial length L1 that is less than the total axial length L of void 156. Second portion 159b extends in an axial direction between base end 153 and first portion 159a. First portion 159a extends in an axial direction between second portion 159b and a midsection 160 of body 151.

First portion 159a forms a collapsible segment CS of body 152 that deforms when piston 150 moves to the open state. Collapsible segment CS is configured to buckle and collapse when male Luer portion L is inserted into first opening 115 and exerts axial compressive force on piston 150, such that sealing end 157 moves out of the first opening, as shown in FIG. 6B. Once the injection is completed and male Luer portion L is removed from first opening 115, the resiliency of wall section 159 causes collapsible segment CS to spring back to its original shape shown in FIG. 6A.

To control retrograde, piston 150 includes a retrograde-reducing stiffener 170 in second portion 159b. Second portion 159b has a wall thickness that is greater than the minimum wall thickness in first portion 159a. The greater wall thickness of second portion 159b resists radial deformation or buckling, and thereby acts as the retrograde-reducing stiffener 170 to prevent deformation in response to incidental changes in pressure caused by a patient's sudden movement, the patient's blood pressure/pulse, an impact force, diffusion, or other events. In this arrangement, retrograde-reducing stiffener 170 prevents or substantially prevents retrograde, while not interfering with the piston's ability to collapse axially and move to the open state during an injection.

Areas of minimum wall thickness according to the present disclosure can have a variety of geometric configurations. In the present example, inner surface 152 of first portion 159a defines a fluted section 161. Fluted section 161 has a radial array of axial slots 162 that extend parallel to longitudinal axis Y of piston 150. Each axial slot 162 defines a wing-shaped recess 164 extending radially outwardly from longitudinal axis Y. Fluted section 161 has areas of minimum wall thickness 163 at each wing-shaped recess 164 that are arranged uniformly around the circumference of first portion 159a. The areas of minimum wall thickness 163 are configured to buckle or deform in response to external force exerted on sealing end 157 so as to allow first portion 159a to buckle or collapse.

Void 156 extends from base end 153 to midsection 160 of piston 150. As such, retrograde-reducing stiffener 170 extends between base end 153 and fluted section 161. Fluted section 161, in turn, extends between retrograde-reducing stiffener 170 and midsection 160. The radially inward taper of inner surface 152 creates a frustoconical-shaped wall geometry 165. Frustoconical-shaped wall geometry 165 extends from second portion 159b into first portion 159a, where it extends between wing-shaped recesses 164.

The axial lengths of the wall sections are carefully selected to provide a specific amount of collapsible length and a specific amount of retrograde-reducing stiffener length. For example, the axial length L1 of first portion 159a is slightly less than the axial length L2 of second portion 159b. The relative lengths of first portion 159a and second portion 159b result in significant collapsibility in the upper portion of piston 150 and significant rigidity in the lower portion of the piston, as seen from the perspective in FIG. 6B. The collapsibility in the upper portion and rigidity in the lower portion achieve the need for a deformable piston element and the competing need for a retrograde-resistant NFC.

In use, NFC 100 is connected to intravenous line IL in a first step by connecting second end 118 of body 110 to intravenous line IL. A fluid source S is then connected to first end 114 by screwing the fluid source onto the first end. As fluid source S is screwed onto first end 114, the male Luer portion L or nozzle on the fluid source enters throat section 112 of body 110 and pushes sealing end 157 of piston 150 downwardly to unseal first opening 115. This displacement moves piston 150 from the sealed state to the open state, in which the piston is collapsed under stored energy. Fluid from fluid source S is then injected into first end 114. The injected fluid flows into fluid passage 102 as shown in FIG. 6B. The fluid flows around piston 150, through fluid passage 102, and out of second opening 119 into intravenous line IL and catheter C.

Once the injection is complete, fluid source S is disconnected from first end 114 of body 110. In the present embodiment, fluid source S is disconnected from body 110 by unscrewing the fluid source. In other embodiments, the fluid source and valve body can feature a Luer slip configuration, which allows the fluid source to be removed from the valve body by applying axial force to the fluid source. Removal of the fluid source S from body 110 moves the male Luer portion L or nozzle of fluid source S out of first opening 115 and releases the displacement force acting on sealing end 157 of piston 150. Release of the displacement force allows the stored energy in piston 150 to be released and move sealing end 157 back into first opening 115. Piston 150 expands and fully returns to its original shape to seal first end 114, as shown in FIG. 6A.

Figure 7:
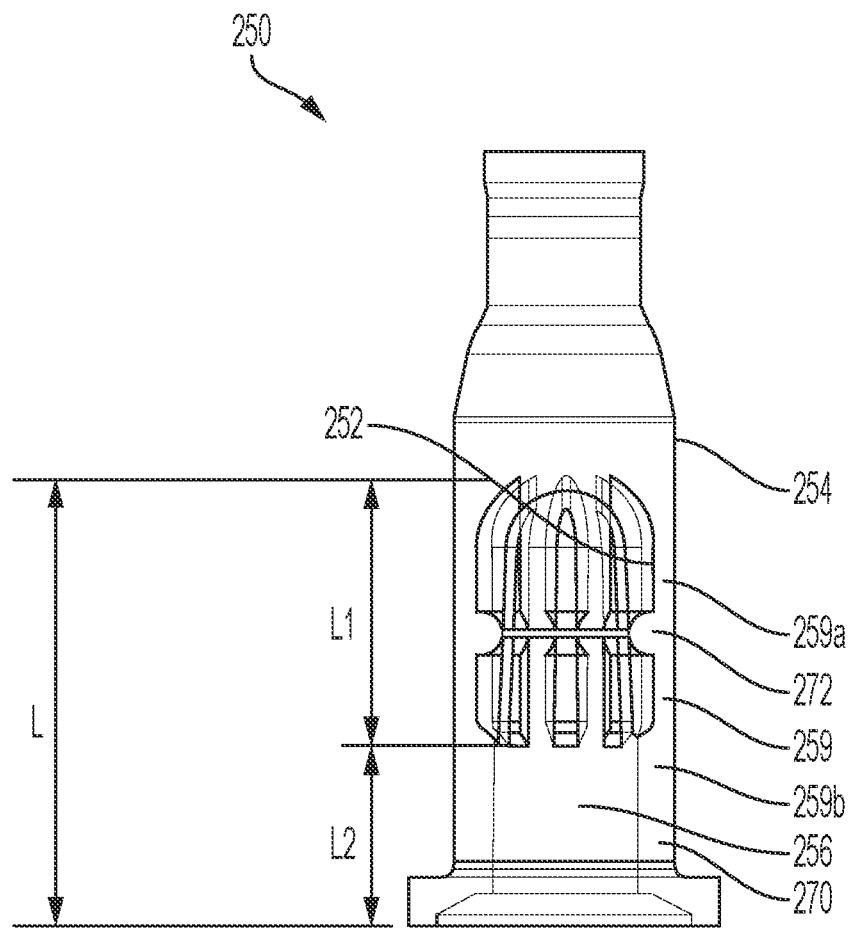
FIG. 7 is an elevation view of a piston element according to another example.

Referring now to FIG. 7, a hollow piston 250 is shown according to another embodiment. Piston 250, which is shown with a transparent wall to illustrate interior features, has the same or substantially the same external geometry as piston 150, and is therefore insertable into and usable with body 110. Many of the features of piston 150 are identical or substantially identical to corresponding features in piston 250.

Piston 250 has an inner surface 252 and an outer surface 254. Inner surface 252 and outer surface 254 define a wall section 259 that circumferentially surrounds a void 256. Wall section 259 has a first portion 259a with areas of minimum wall thickness, and a second portion 259b. Second portion 259b has a wall thickness significantly greater than the minimum wall thickness, forming a retrograde-reducing stiffener 270 that prevents or substantially prevents retrograde, while not interfering with the piston's ability to move to the open state.

First portion 259a has an axial length L1 that is less than a total axial length L of void 256. Unlike the previous embodiment, axial length L1 of first portion 259a is slightly greater than the axial length L2 of second portion 259b. The collapsibility of first portion 259a is tempered or counterbalanced by an annular wall section or ring 272. Ring 272 has a wall thickness greater than or substantially equal to the maximum wall thickness of second portion 259b. As such, ring 272 acts as an extension of retrograde-reducing stiffener 270.

Figure 8:
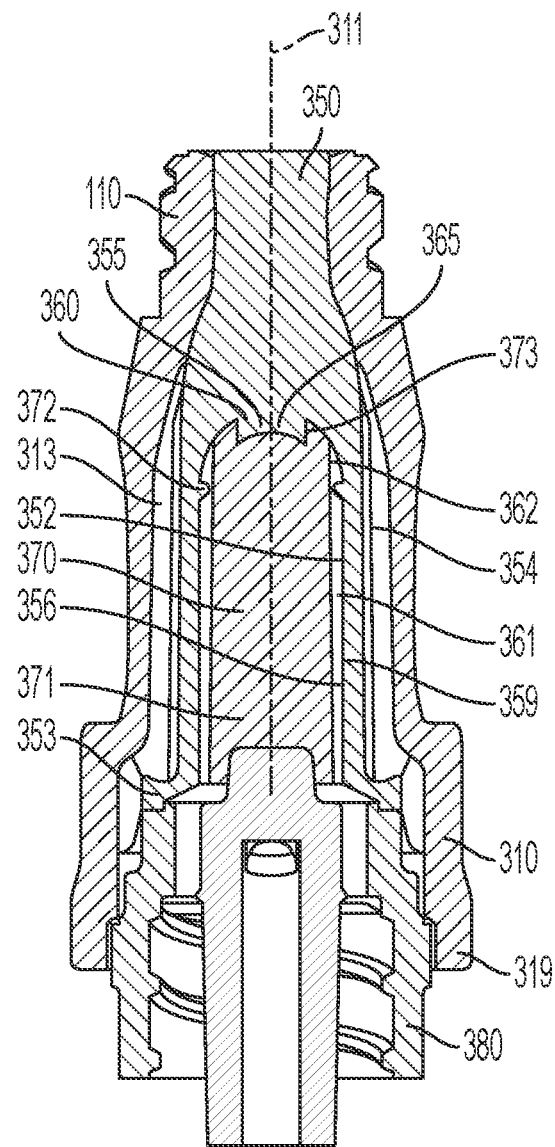
FIG. 8 is a cross section view of an NFC and piston element according to another example.

Referring now to FIG. 8, a hollow piston 350 is shown according to another embodiment. Piston 350 has the same or substantially the same external geometry as piston 150, and is therefore insertable into and usable with body 110, as shown. Many of the features of piston 350 are identical or substantially identical to corresponding features in piston 150.

Piston 350 has an inner surface 352 and an outer surface 354. Inner surface 352 and outer surface 354 define a wall section 359 that circumferentially surrounds a void 356. Unlike the previous embodiments, wall section 359 is not divided into two sections with different wall thicknesses to promote either collapsibility or rigidity, depending on wall thickness. Instead, wall section 359 has a generally constant profile along the length of void 356.

Inner surface 352 defines a fluted surface 361 having a radial array of axial slots 362 that extend parallel to longitudinal axis 311 of piston 350. Fluted surface 361 and axial slots 362 extend from base end 353 of piston 350 to midsection 360. Therefore, fluted surface 361 and axial slots 362 extend the entire length of void 356. This creates areas of minimum wall thickness along the entire length of void 356 that provide a degree of collapsibility in wall section 359.

To resist or prevent retrograde, a retrograde-reducing stiffener 370 is positioned inside void 356 and extends the entire length of the void. Retrograde-reducing stiffener 370 is a resilient member with a cylindrical body 371. Cylindrical body 371 has a large length to diameter ratio. In this configuration, retrograde-reducing stiffener 370 provides little resistance to axial collapse in a direction parallel to longitudinal axis 311. The small resistance to axial collapse allows the piston to move from the sealing state to the open state.

Retrograde-reducing stiffener 370 also provides resistance to buckling in a radial direction, i.e. the direction perpendicular to longitudinal axis 311. The resistance to radial buckling is sufficient to resist or prevent the piston wall from buckling or collapsing in response to incidental changes in fluid pressure in chamber 313 that are caused by a patient's sudden movement, the patient's blood pressure/pulse, an impact force, diffusion, or other events. As such, retrograde-reducing stiffener 370 prevents or substantially prevents retrograde, while not interfering with the piston's ability to move to the open state. Retrograde-reducing stiffener 370 can be made of a variety of materials that allow the piston to collapse when needed but resist or prevent retrograde. For example, retrograde-reducing stiffener 370 can be made of a polyurethane or foam material.

Cylindrical body 371 is stabilized and centered in void 356 by an annular ring 372. Annular ring 372 adds a small amount of wall thickness and rigidity to wall section 359, similar to annular ring 272, but need not be a primary contributor to rigidity and retrograde reduction.

A Luer adapter 380 is connected to second end 319 of body 310. Cylindrical body 371 is captively held between Luer adapter 380 and closed end 365 of void 356. In this arrangement, cylindrical body 371 is axially fixed in void 356. Cylindrical body 371 has a notch 373 at one end that receives a projection 355 at closed end 365 of void 356. Notch 373 receives projection 355 in a snug fit to further stabilize and center cylindrical body 371 inside piston 350.

Although this description makes reference to specific embodiments and illustrations, the present disclosure is not intended to be limited to the details shown. Accordingly, the present disclosure encompasses various modifications and combinations of the specific embodiments and illustrations described herein, including variations that may be made within the scope and range of equivalents of the originally filed claims.

What is claimed is:
1. A needle-free connector for accessing a patient's intravenous line, the needle-free connector comprising:
    a hollow body having a first end with a first opening, a second end with a second opening, and an inner wall defining a chamber; and
    a hollow piston disposed in the chamber, the hollow piston comprising an inner surface, an outer surface, a longitudinal axis and a void inside the hollow piston,
    the hollow piston being axially collapsible in the chamber to allow fluid to flow between the inner wall of the hollow body and the outer surface of the hollow piston,
    the inner surface of the hollow piston forms an annular ring that extends radially inwardly from the inner surface, the inner surface of the hollow piston comprising a fluted section having a radial array of axial slots that extend parallel to the longitudinal axis, the fluted section having a first radial thickness that is configured to buckle in response to axial force applied to the hollow piston, the hollow piston further comprising a retrograde-reducing stiffener, the retrograde-reducing stiffener having a second radial thickness that is greater than the first radial thickness.

2. The needle-free connector of claim 1, wherein each axial slot defines a wing-shaped recess extending radially outwardly from the longitudinal axis.

3. The needle-free connector of claim 1, wherein the void extends from a base end of the hollow piston to a midsection of the hollow piston.

4. The needle-free connector of claim 3, wherein the inner surface of the hollow piston and the outer surface of the hollow piston define a wall section that circumferentially surrounds the void.

5. The needle-free connector of claim 4, wherein the fluted section comprises a first portion of the wall section, and the retrograde-reducing stiffener comprises a second portion of the wall section.

6. The needle-free connector of claim 5, wherein the retrograde-reducing stiffener extends between the base end of the hollow piston and the fluted section.

7. The needle-free connector of claim 3, wherein the fluted section extends from the base end of the hollow piston to the midsection of the hollow piston.

8. The needle-free connector of claim 7, wherein the retrograde-reducing stiffener comprises a resilient member housed inside of the void.

9. The needle-free connector of claim 8, wherein the resilient member is made of foam.

10. The needle-free connector of claim 8, wherein the resilient member is cylindrical.

11. The needle-free connector of claim 10, wherein the resilient member has an axial length and a diameter, the axial length being greater than the diameter.

12. The needle-free connector of claim 3, wherein the hollow piston comprises a sealing end opposite the base end.

13. The needle-free connector of claim 12, wherein the sealing end is movable in the chamber to a sealing state in which the sealing end fluidly seals the first opening of the hollow body to prevent fluid flow through the first end.

14. The needle-free connector of claim 13, wherein the sealing end is movable out of the sealing state and into an open state, the sealing end being moved away from the first opening in the open state to permit fluid flow through the first end.

15. The needle-free connector of claim 12, wherein the sealing end comprises at least one slit that opens in response to axial force applied to the hollow piston.

16. The needle-free connector of claim 1, wherein the hollow body is made of thermoplastic resin.

17. The needle-free connector of claim 1, wherein the hollow piston is made of silicon rubber.

18. The needle-free connector of claim 1, wherein the annular ring comprises at least a portion of the retrograde-reducing stiffener.

19. The needle-free connector of claim 1, wherein the inner surface tapers radially inwardly toward the longitudinal axis along a length of the void.

20. A needle-free connector for accessing a patient's intravenous line, the needle-free connector comprising:

a hollow body having a first end with a first opening, a second end with a second opening, and an inner wall defining a chamber; and a hollow piston disposed in the chamber, the hollow piston comprising an inner surface, an outer surface, a longitudinal axis and a void inside the hollow piston, the hollow piston being axially collapsible in the chamber to allow fluid to flow between the inner wall of the hollow body and the outer surface of the hollow piston, wherein the void extends from a base end of the hollow piston to a midsection of the hollow piston, the inner surface of the hollow piston comprising a fluted section having a radial array of axial slots that extend parallel to the longitudinal axis, the fluted section having a first radial thickness that is configured to buckle in response to axial force applied to the hollow piston, wherein the fluted section extends from the base end of the hollow piston to the midsection of the hollow piston, the hollow piston further comprising a retrograde-reducing stiffener, the retrograde-reducing stiffener having a second radial thickness that is greater than the first radial thickness, wherein the retrograde-reducing stiffener comprises a resilient member housed inside of the void.

21. The needle-free connector of claim 20, wherein each axial slot defines a wing-shaped recess extending radially outwardly from the longitudinal axis.

22. The needle-free connector of claim 20, wherein the inner surface of the hollow piston and the outer surface of the hollow piston define a wall section that circumferentially surrounds the void.

23. The needle-free connector of claim 22, wherein the fluted section comprises a first portion of the wall section, and the retrograde-reducing stiffener comprises a second portion of the wall section.

24. The needle-free connector of claim 23, wherein the retrograde-reducing stiffener extends between the base end of the hollow piston and the fluted section.

25. The needle-free connector of claim 20, wherein the resilient member is cylindrical.

26. The needle-free connector of claim 25, wherein the resilient member has an axial length and a diameter, the axial length being greater than the diameter.

27. The needle-free connector of claim 20, wherein the hollow piston comprises a sealing end opposite the base end.

28. The needle-free connector of claim 27, wherein the sealing end is movable in the chamber to a sealing state in which the sealing end fluidly seals the first opening of the hollow body to prevent fluid flow through the first end.

29. The needle-free connector of claim 28, wherein the sealing end is movable out of the sealing state and into an open state, the sealing end being moved away from the first opening in the open state to permit fluid flow through the first end.

30. The needle-free connector of claim 27, wherein the sealing end comprises at least one slit that opens in response to axial force applied to the hollow piston.

\* \* \* \* \*